(12) United States Patent
Okano et al.

(10) Patent No.: US 8,257,920 B2
(45) Date of Patent: Sep. 4, 2012

(54) METHOD OF DETECTING ACTIVATION OF NOTCH SIGNAL TRANSMISSION SYSTEM

(75) Inventors: Hideyuki Okano, Tokyo (JP); Akinori Tokunaga, Fukuoka (JP); Jun Kohyama, Kizugawa (JP); Keiko Nakao, Asaka (JP)

(73) Assignee: Keio University, Tokyo (JP)

( * ) Notice: Subject to any disclaimer, the term of this patent is extended or adjusted under 35 U.S.C. 154(b) by 876 days.

(21) Appl. No.: 11/665,264

(22) PCT Filed: May 10, 2005

(86) PCT No.: PCT/JP2005/008505
§ 371 (c)(1),
(2), (4) Date: Jul. 23, 2009

(87) PCT Pub. No.: WO2006/040854
PCT Pub. Date: Apr. 20, 2006

(65) Prior Publication Data
US 2009/0305320 A1    Dec. 10, 2009

(30) Foreign Application Priority Data
Oct. 12, 2004 (JP) .................. 2004-298241

(51) Int. Cl.
*C07H 21/04* (2006.01)
*C12N 5/00* (2006.01)
*C12N 15/00* (2006.01)
*C12N 15/09* (2006.01)
*C12Q 1/68* (2006.01)

(52) U.S. Cl. ...... 435/6.1; 435/320.1; 435/325; 536/23.1

(58) Field of Classification Search .................. None
See application file for complete search history.

(56) References Cited

U.S. PATENT DOCUMENTS

| 7,264,793 B2 * | 9/2007 | Imai et al. ................. 424/9.1 |
| 2003/0181380 A1 * | 9/2003 | Pear et al. ................. 514/12 |
| 2005/0025751 A1 * | 2/2005 | Bodmer et al. ............ 424/93.21 |

FOREIGN PATENT DOCUMENTS
WO    WO-03012441 A1 *  2/2003

OTHER PUBLICATIONS

Jarriault et al. Delta-1 activation of Notch-1 signaling results in Hes-1 transactivation. Mol Cell Biol 18(12): 7423-7431, 1998.*
Shimizu et al. Functional diversity among Notch1, Notch2, and Notch3 receptors. Biochem Biophys Res Comm 4: 775-779, 2002.*
Campbell et al. Totipotency of multipotentiality of cultured cells: applications and progress. Theriogenology 47: 63-72, 1997.*
Kaufman et al. Blood 94: 3178-3184, 1999.*
Wang et al. Rapid analysis of gene expression (RAGE) facilitates universal expression profiling. Nucleic Acids Res 27(23): 4609-4618, 1999.*
Wigley et al. Site-specific transgene insertion: an approach. Reprod Fertil Dev 6: 585, 588, 1994.*
McBurney et al. Evidence for repeat-induced gene silencing in cultured mammalian cells: inactivation of tandem repeats of transfected genes. Exp Cell Res 274: 1-8, 2002.*
Williams et al. BMC Biotech 5: 17, 2005 (9 total pages).*
Tokunaga, Akinori et al., "Mapping Spatio-Temporal Activation of Notch Signaling During Neurogenesis and Gliogenesis in the Developing Mouse Brain", Journal of Neurochemistry, 2004, 90, pp. 142-154.
Yamamoto, Naoya et al., "Role of Deltex-1 as a Transcriptional Regulator Downstream of the Notch Receptor", The Journal of Biological Chemistry, vol. 276, No. 48, (2001), pp. 45031-45040.
Miyoshi, Hiroyuki et al., "Development of a Self-Inactivating Lentivirus Vector", Journal of Virology, Oct. 1998, p. 8150-8157, vol. 72, No. 10.
Kawaguchi, Ayano et al., "Nestin-EGFP Transgenic Mice: Visualization of the Self-Renewal and Multipotency of CNS Stem Cells", Molecular and Cellular Neuroscience, vol. 17, pp. 259-273 (2001).
Jarriault et al., "Signalling Downstream of Activated Mammalian Notch", Nature, vol. 377, No. 6547, pp. 355-358, (1995).
Nagai et al., "A Variant of Yellow Fluorescent Protein With Fast and Efficient Maturation for Cell-Biological Applications", Nature Biotechnology, vol. 20, No. 1, pp. 87-90, (2002).
Leclerc et al., "Development of a Destabilized Firefly Luciferase Enzyme for Measurement of Gene Expression", Biotechniques, vol. 29, No. 3, pp. 590-601, (2000).
Li et al., "Generation of Destabilized Green Fluorescent Protein as a Transcription Reporter", J. Biol. Chem., vol. 273, No. 52, pp. 34970-34975, (1998).
Li et al., "*Improved Isolation and Culture of Embryonic Stem Cells from Chinese Miniature Pigs*," Journal of Reproduction and Development, vol. 5, No. 2, Apr. 2004.
Online version of Chapter 8 from Molecular Biology of the Cell. 4th edition. Alberts B, Johnson A, Lewis J, et al. New York: Garland Science; 2002.; available online at www.ncbi.nlm.nih.gov/books/NBK21054 (last visited May 31, 2011).

* cited by examiner

*Primary Examiner* — Bridget E Bunner
(74) *Attorney, Agent, or Firm* — Finnegan, Henderson, Farabow, Garrett & Dunner, LLP

(57) ABSTRACT

The purpose of the present invention is to provide detection methods of Notch signaling activation for detecting the activation of the Notch signaling in living cells simply and conveniently. The expression of a fluorescent protein Venus in a transgenic cell into which a vector having the fluorescent protein Venus gene which is controlled by the wild-type Hes-1 gene promoter has been introduced is compared with the expression of a fluorescent protein Venus in a transgenic cell into which a vector having the fluorescent protein Venus gene controlled by a mutated Hes-1 gene promoter which is not controlled by an activated Notch protein has been introduced, and a transgenic cell in which a signal by the expression of Venus introduced by the vector having the wild-type Hes-1 promoter is observed and in which a signal by the expression of Venus introduced by the vector having the mutated Hes-1 gene promoter which is not controlled by the activated Notch protein is not observed is identified.

12 Claims, 7 Drawing Sheets

Hes1 promoter sequence (G)ATTAATCTCAGGGCGGCCATTGGCCGCCAGACCTTGTGCCTAGCGGCCAATGGGGGGCCAGTCCACGAGCGGTGCCGCGTG
AseI  Primer 1

TCTCTTCCTCCCATTGGCTGAAAGTTACTGTGGGAAAGAAAAGTTTGGGAAGTTTCACACGAGCCGTTCGGTGTGCAGTCCCAGATATAT
              <CTGGGAA>                              <TTCACTC>
           RBP-J binding sequence              RBP-J binding sequence ATAGAGGCCGCCAGGGCCTGGGATCACACAGGATCTGAGCTGGTGCTGATAACAGCGGAATCCCTGTGCTACCTCTCCTCCTTGTCC TGGGATAGTGCTACCGATCACTAAGTAGCCCTAAGACTATATAATAAACCTTCAACTGCTCAGTAGTTTTTCTTATGAAAGTCAAGTAAAA GGACGTAAGCGGGATCC(ACCGGTC)
Primer 2        AgeI

METHOD OF DETECTING ACTIVATION OF NOTCH SIGNAL TRANSMISSION SYSTEM

CROSS REFERENCE TO RELATED APPLICATIONS

This application claims the benefit of priority to Japan Patent Application No. 2004-298241, filed on Oct. 12, 2004, which is incorporated herein by reference.

TECHNICAL FIELD

The present invention relates to methods for detecting Notch signaling activation, and gene-transferred cells and reporters to be used therefore.

BACKGROUND ART

The Notch signaling regulates various biological functions centering around developmental processes. Although Notch, a transmembrane protein, is extensively expressed, the Notch signaling is not activated in all cells, because the Notch signaling is activated by a signal being transmitted from Delta present on a neighboring cell membrane.

Several experiments have been conducted to detect the activation of the Notch signaling. For example, since the activation of the Notch signaling eventually leads to transactivation of Hes-1 gene in a nucleus, by using the activation of Hes-1 promoter as an indicator of the activation of Notch signaling, luciferase was made to be expressed under the control of the HES-1 promoter according to the activation of Notch signals (Jarriault, S., Brou, C., Logeat, F., Schroeter, E. H., Kopan, R. and Israel, A. (1995) Signalling downstream of activated mammalian Notch. Nature 377, 355-8.). It is also the case for immunohistochemical staining performed using an antibody against activated Notch1, (Tokunaga A. Kohyama, J., Yoshida, and T., Nakao, K., Sawamoto, K., and Okano, H. (2004). Mapping spatio-temporal activation of Notch signaling during neurogenesis and gliogenesis in the developing mouse brain. J. Neurochem. 90, 142-154.). These approaches have made it possible to detect the activation of the Notch signaling.

DISCLOSURE OF THE INVENTION

Problems to be Solved by the Invention

However, since the HES promoter contains a region which is regulated by signaling pathways other than the Notch signaling, the activation of the HES promoter does not exactly reflect this activation, by using solely the wild-type Hes-1 promoter as an indicator of the Notch signaling activation. In addition, it is technically difficult to detect Notch signaling activation by immunohistochemical approach with antibodies specific to the activated Notch. Moreover, in the previously developed methods, homogenization or fixation of cells was required; therefore it was impossible to detect the activation of the Notch signaling Thus, the present invention was accomplished to provide detection methods of Notch signaling activation for detecting the activation of the Notch signaling in living cells conveniently, as well as gene-transferred cells and fluorescent protein expression reporters to be used for such detection.

Means for Solving the Problems

The detection method of Notch signaling activation according to the present invention is a method for detecting a cell in which the Notch signaling is activated, including the steps of comparing the expression of a first fluorescent protein in a transgenic cell, the cell having a first fluorescent protein (FP) gene encoding the first fluorescent protein and being controlled by a wild-type Hes-1 gene promoter with the expression of a second fluorescent protein in the transgenic cell, the cell having a second fluorescent protein (FP) gene encoding the second fluorescent protein and being controlled by a mutated Hes-1 gene promoter, the mutated promoter being not controlled by an activated Notch 1 protein, and identifying a cell in which a signal by the expression of the first fluorescent protein is observed but a signal by the expression of the second fluorescent protein is not observed.

In the above-mentioned method of the Notch signaling activation, at least one of the first fluorescent protein gene and the second fluorescent protein gene may be inserted into a Hes-1 locus and controlled by the endogenous Hes-1 gene promoter in the Hes-1 locus. Alternatively, at least one of the first fluorescent protein gene and the second fluorescent protein gene may be controlled by an exogenous Hes-1 gene promoter inserted into the genome.

The endogenous Hes-1 gene promoter in a Hes-1 locus herein refers to an intrinsic Hes-1 gene promoter on the genome of an organism, but its sequence per se may be substituted with an exogenous sequence. For example, an endogenous Hes-1 gene promoter intrinsically located on a Hes-1 locus may be substituted with an exogenous wild-type Hes-1 gene promoter or with an exogenous mutated Hes-1 gene promoter by homologous recombination, because as long as the overall structure is the same, there is no difference in the promoter function and thus the expression of the intrinsic Hes-1 gene can be reproduced.

In any of the above-described detection methods of Notch signaling activation, it is preferred that the mutated Hes-1 gene promoter has a mutation in an RBP-J binding sequence. In addition, it is preferred that at least one of the first fluorescent protein and the second fluorescent protein is Venus. Further, in any of the above-described detection methods of Notch signaling activation, a PEST sequence may be fused with at least one fluorescent protein of the first fluorescent protein and the second fluorescent protein.

A PEST sequence refers to an amino acid sequence which is rich in proline-glutamic acid-serine-threonine with no specificity in its sequence or length, having a function of reducing the half-life of a protein in a cell.

Further, the pair of cells according to the present invention consists of a first transgenic cell having a first fluorescent protein (FP) gene controlled by a wild-type Hes-1 gene promoter, and a second transgenic cell having a second fluorescent protein gene controlled by a mutated Hes-1 gene promoter, the mutated promoter being not controlled by an activated Notch protein. Also, the gene-transferred cell according to the present invention has a first fluorescent protein (FP) gene controlled by a wild-type Hes-1 gene promoter and a second fluorescent protein gene controlled by a mutated Hes-1 gene promoter, the mutated promoter being not controlled by an activated Notch protein. The difference between these aspects lies in that, while in the former the first fluorescent protein gene controlled by the Hes-1 gene promoter and the second fluorescent protein gene controlled by the mutated Hes-1 gene promoter are introduced into different cells, in the latter they are introduced into the same cell.

The gene-transferred cell may be present alone like cultured cells, or may form a cell population, such as a tissue, an organ, and an individual together with other cells.

In the above-mentioned pair of cells or the gene-transferred cells, at least one fluorescent protein gene of the first fluorescent protein gene and the second fluorescent protein gene may be inserted into a Hes-1 locus and controlled by the endogenous Hes-1 gene promoter in the Hes-1 locus. Alternatively, at least one fluorescent protein gene of the first fluorescent protein gene and the second fluorescent protein gene may be controlled by an exogenous Hes-1 gene promoter inserted into the genome.

In the above-mentioned pair of cells or the gene-transferred cell, it is preferred that the mutated Hes-1 gene promoter has a mutation in an RBP-J binding sequence. Further, it is preferred that the fluorescent protein encoded by at least one fluorescent protein gene of the first fluorescent protein gene and the second fluorescent protein gene is Venus. A PEST sequence may be fused with the fluorescent protein encoded by at least one fluorescent protein gene of the first fluorescent protein gene and the second fluorescent protein gene.

The pair of fluorescent protein expression reporters according to the present invention consists of a first fluorescent protein expression reporter constructed such that the expression of a first fluorescent protein gene is controlled by a wild-type Hes-1 gene promoter, and a second fluorescent protein expression reporter constructed such that the expression of a second fluorescent protein gene is controlled by a mutated Hes-1 gene promoter, the mutated promoter being not controlled by an activated Notch protein.

In the above-mentioned pair of reporters, it is preferred that the mutated Hes-1 gene promoter has a mutation in an RBP-J binding sequence. Further, in either of the pair of fluorescent protein expression reporters, it is preferred that the fluorescent protein encoded by the fluorescent protein gene is Venus. A PEST sequence may be fused with the fluorescent protein encoded by either of the fluorescent protein genes.

BRIEF DESCRIPTION OF THE DRAWINGS

FIG. 2 shows the nucleotide sequences and structures of the Hes-1 promoters (wild-type (SEQ ID NO: 3) and mutated (SEQ ID NO: 4)) used in the Example according to the present invention. The RBP-J binding sequences are double underlined. The sequence in angled brackets < > indicates the nucleotide sequence of the mutated Hes-1 promoter (Hes1pAmBm) (SEQ ID NO: 4). The primer sequences used for preparation of pHes1 p-d4Venus are single underlined. It should be noted that the sequence in brackets ( ) indicates the sequence which is not present in the original promoter but has been added for cloning. The recognition sequence of each restriction enzyme is emphasized in bold.

FIG. 8A shows results for Hes1p-Venus (wild-type Hes-1 promoter) and FIG. 8B shows results for Hes1pAmBm-Venus (mutated Hes-1 promoter).

BEST MODE FOR CARRYING OUT THE INVENTION

Figure 1:
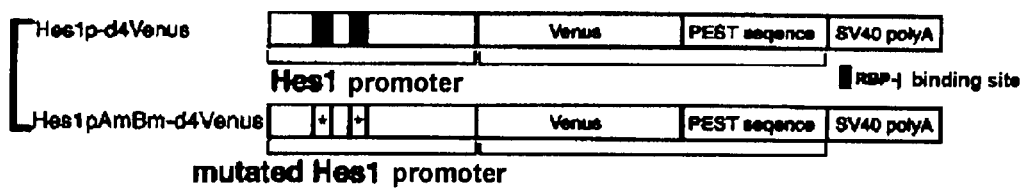
FIG. 1 shows structures of pHes1 p-d4Venus and pHes1 pAmBm-d4Venus used in the Example according to the present invention.

Embodiments of the present invention accomplished based on the above-described findings are hereinafter described in detail by giving Examples. Unless otherwise explained, methods described in standard sets of protocols such as J. Sambrook and E. F. Fritsch & T. Maniatis (Ed.), "Molecular Cloning, a Laboratory Manual (3rd edition), Cold Spring Harbor Press and Cold Spring Harbor, N.Y. (1989); and F. M. Ausubel, R. Brent, R. E. Kingston, D. D. Moore, J. G. Seidman, J. A. Smith, and K. Struhl (Ed.), "Current Protocols in Molecular Biology," John Wiley & Sons Ltd., or their modified/changed methods are used. When using commercial reagent kits and measuring apparatus, unless otherwise explained, protocols attached to them are used.

The object, characteristics, and advantages of the present invention as well as the idea thereof will be apparent to those skilled in the art from the descriptions given herein. It is to be understood that the embodiments and specific examples of the invention described hereinbelow are to be taken as preferred examples of the present invention. These descriptions are only for illustrative and explanatory purposes and are not intended to limit the invention to these embodiments or examples. It is further apparent to those skilled in the art that various changes and modifications may be made based on the descriptions given herein within the intent and scope of the present invention disclosed herein.

==Preparation of Gene-Transferred Cells Having a Fluorescent Protein Gene==

Gene-transferred cells which have a first fluorescent protein gene controlled by a wild-type Hes-1 gene promoter and/or a second fluorescent protein gene controlled by a mutated Hes-1 gene promoter which is not controlled by an activated Notch protein are prepared.

The fluorescent protein is not limited as long as it emits fluorescence when excited by a specific wavelength. Such fluorescent proteins illustratively include green fluorescent proteins (GFPs), yellow fluorescent proteins (YFPs), blue fluorescent proteins (BFPs), etc., among which Venus, an improved variant of YFP, is preferred because of its high fluorescence intensity. Venus is a protein designed by introducing point mutations into a YFP to have a very high fluorescence intensity and shortened chromophore formation time as compared with the conventional fluorescent proteins (Nagai et al., Nat. Biotechnol. 20, 87-90, 2002).

The first fluorescent protein and the second fluorescent protein may be the same kind or different kinds of protein. In introducing both fluorescent proteins into the same cell and comparing the signals in the cell, different kinds of fluorescent proteins should be used.

The gene-transferred cells may be prepared as a cultured cell line, and may be cells in a tissue or an organ or in a transgenic mouse.

The mutation in the mutated Hes-1 gene promoter is not limited as long as it results in loss of activation of the mutated promoter by Notch signaling. One example is a mutation in an RBP-J binding sequence, which prevents binding of the RBP-J protein. In this case, it is preferred that the mutated Hes-1 gene promoter has the identical nucleotide sequence to the wild-type Hes-1 gene promoter except for the introduced mutation, so as not to change all regulations of the promoter by signals other than the Notch signaling. Further, to minimize the influence on promoter controls by other signals than the Notch signaling, smaller mutation to be introduced is more preferable, and a point mutation is the most preferable.

==Use of the Endogenous Hes-1 Gene Promoter==

The fluorescent protein gene to be controlled by the Hes-1 gene promoter is preferred to be inserted into the Hes-1 locus and controlled by an endogenous Hes-1 gene promoter intrinsic to the Hes-1 locus in the genome in order to be controlled as correctly as in vivo. In this case, by using the technique of homologous recombination, a fluorescent protein gene can be inserted into the Hes-1 locus or can be substituted with the endogenous Hes-1 gene. Likewise, by using the technique of homologous recombination, a mutation can be introduced into the endogenous Hes-1 gene promoter.

In the above case, cells to be used are not particularly limited; for construction of transgenic mice, for example, embryonic stem cells are used. In this case, transgenic mice can be obtained by generating germline chimeric mice and isolating mice having the genome which has undergone homologous recombination by using conventional methods. In addition, by subjecting tissues, organs, and cells of these transgenic mice to culture, transgenic tissues, organs, and cells can be obtained.

==Use of the Exogenous Hes-1 Gene Promoter==

The fluorescent protein gene may be controlled by the exogenous Hes-1 gene promoter inserted outside the Hes-1 locus. That is, an expression vector into which a fluorescent protein gene has been inserted under the control of the Hes-1 gene promoter may be constructed and introduced into cells. The details are described as follows.

First, by inserting a fluorescent protein gene downstream of the wild-type Hes-1 gene promoter, a first fluorescent protein expression reporter in which a fluorescent protein is expressed by the activation of the Notch signaling is constructed. The wild-type Hes-1 gene promoter may be any region that has an RBP-J binding sequence and is activated by the activation of the Notch signaling, but the most preferred is a region which undergoes the same regulation as an endogenous Hes-1 gene promoter does. The wild-type Hes-1 gene promoter may or may not contain a minimal promoter, the minimal region required for transcription of a downstream gene. When the minimal promoter is not contained, a minimal promoter of another gene is used. The origin of the minimal promoter can include, but is not limited to, SV40, tk, actin, etc.

Next, by inserting a fluorescent protein gene downstream of a mutated Hes-1 gene promoter, a second fluorescent protein expression reporter in which the fluorescent protein is not expressed by the activation of the Notch signaling is constructed. The mutated Hes-1 gene promoter may or may not contain a minimal promoter, the minimal region required for transcription of a downstream gene. When the minimal promoter is not contained, a minimal promoter of another gene is used. The origin of the minimal promoter can include, but is not limited to, SV40, tk, actin, etc.

Preferably, the first fluorescent protein expression reporter and the second fluorescent protein expression reporter have identical nucleotide sequence except for the mutation introduced into the Hes-1 gene promoter. However, their sequences may be different as long as the promoter on the first fluorescent protein expression reporter is activated by the activation of the Notch signaling while the promoter on the second fluorescent protein expression reporter is not activated by the activation of the Notch signaling; and that the other promoters of both the reporters are regulated in the same way.

These first fluorescent protein expression reporter and the second fluorescent protein expression reporter may be either on one vector or on different vectors when introduced into the same cell, but they must be on different vectors when introduced into different cells.

Gene-transferred cells are prepared by using the fluorescent protein expression reporters constructed as described above. For example, a vector which has a fluorescent protein expression reporter can be introduced into cultured cells (including cultured tissues and cultured organs) using the conventional methods, such as lipofection, transfection, electroporation, etc. In this case, a plasmid is preferably used for the vector. Alternatively, the fluorescent protein expression reporter may be introduced into cultured cells by viral infection using a viral vector such as adenoviruses and retroviruses. Transgenic mice can be constructed using the fluorescent protein expression reporter by conventional methods.

==Detection of the Notch Signaling Activation==

Using cells of the same cell type, gene-transferred cells which have a first fluorescent protein (FP) gene encoding the first fluorescent protein and being controlled by the wild-type Hes-1 gene promoter, and gene-transferred cells which have a second fluorescent protein (FP) gene encoding the second fluorescent protein and being controlled by a mutated Hes-1 gene promoter which is not controlled by an activated Notch 1 protein are prepared, as described above, and the expression of the first fluorescent protein is compared with that of the second fluorescent protein. Since the wild-type Hes-1 gene promoter responds to the activation of the Notch signaling and the mutation Hes-1 gene promoter does not respond to the activation of the Notch signaling, it can be determined that the Notch signaling is activated when a signal by the expression of the first fluorescent protein is observed and a signal by the expression of the second fluorescent protein is not observed.

Specifically, for example, a mouse which has the Venus gene controlled by the wild-type Hes-1 gene promoter and a mouse which has the Venus gene controlled by the mutated Hes-1 gene promoter are generated, and fluorescent regions in both mice are compared. Alternatively, both of the first fluorescent protein gene (e.g., GFP gene) controlled by the wild-type Hes-1 gene promoter and the second fluorescent protein gene (e.g., YFP gene) controlled by the mutated Hes-1 gene promoter are introduced into the same mouse, and by identifying a region where only the expression of the GFP is detected, a region where the Notch signaling is activated can be detected.

Signals generated by expression of a fluorescent protein is identified by detecting fluorescence obtained by exciting the cells with light of a suitable wavelength. Since this technique can be used while keeping cells alive and no fixation of cells is required, it is possible, for example, to monitor signals in a mouse with the passage of time. Alternatively, after fixing cells or preparing sections, it is also possible to immunohistologically detect signals by using antibody against the fluorescent protein.

==Detection of Suppression of Expression by the RBP-J Protein==

When the Notch signaling is not activated, a RBP-J protein exerts the function of binding to RBP-J binding site in the wild-type Hes-1 promoter and suppressing promoter activity.

Therefore, in the case of an individual having a promoter carrying a mutation in the RBP-J binding sequence, in cells where the Hes-1 gene expression would be normally suppressed by the RBP-J protein, the suppression of the expression is released and thereby ectopic expression is observed. Thus, a reporter controlled by a mutated Hes-1 gene promoter carrying a mutation in the RBP-J binding sequence can be used to identify cells in which the Hes-1 gene expression is suppressed by the RBP-J protein.

EXAMPLES

Construction of Plasmids

An AgeI-NotI fragment of d4Venus cDNA (Nagai et al., Nat. Biotechnol. 20, 87-90, 2002) was replaced with an AgeI-NotI fragment of pEGFP (Clontech, Inc.) and pEGFP-N1 (Clontech, Inc.) to generate pd4Venus-1 and pd4Venus-1-N1, respectively. The promoter region of Hes1p-luciferase (Jarriaut et al., Nature 377, 355-358, 1995) was amplified by PCR using the following primers having an AseI site or an AgeI site, respectively.

```
                                              (SEQ ID NO: 1)
    Primer 1: GATTAATCTCAGGCGCGCGCCA (SEQ ID NO: 2)
    Primer 2: GACCGGTGGATCCGCTTACGTC
```

A fragment obtained by treating the amplified DNA fragment with the restriction enzymes AseI-AgeI and a (KpnI-HindIII) fragment of Hes1 pAmBm-luciferase (Jarriault et al. Nature 377, 355-358, 1995) were inserted into the AseI-AgeI site of pd4Venus-1-N1 and the KpnI-HindIII site of pd4Venus-1 to generate pHes1 p-d4Venus and pHes1 pAmBm-d4Venus, respectively. FIG. 1 shows the plasmid maps of these constructs.

In pHes1 p-d4Venus, the gene encoding the fluorescent protein Venus fused with a PEST sequence is inserted into the downstream of the Hes-1 promoter (refer to FIG. 2), and the SV40polyA signal is inserted further downstream as a transcriptional termination sequence. This Hes-1 promoter fragment is known to be capable of reflecting correctly the response to the Notch signals in vivo. Further, since a PEST sequence reduces the half-life of Venus, addition of a PEST sequence to Venus eliminates the possibility of detection of Venus after the Venus expression has been lost, thereby strengthening the correlation of expression and detection. Furthermore, the Hes1pAmBm promoter (FIG. 2), a mutated Hes-1 promoter, carries a mutation in two RBP-J binding sequences, which prevents binding of RBP-J (Jarriault et al., Nature 377, 355-358, 1995).

Figure 3:
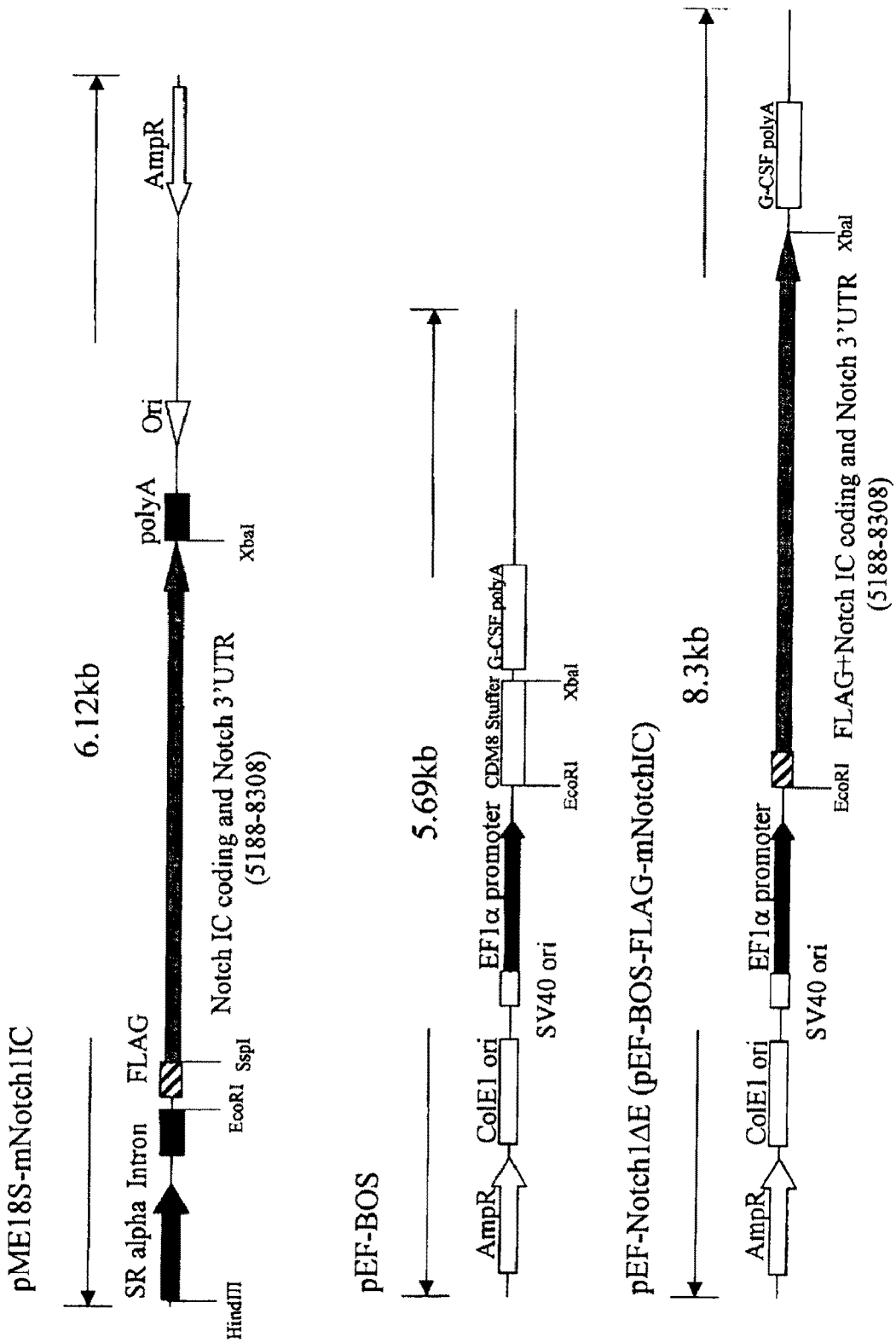
FIG. 3 shows the restriction maps of pME18S-mNotchIC, pEF-BOS, and pEF-Notch1A (pEF-NotchΔE) used in the Example according to the present invention.

An EcoRI-XbaI fragment of pME18 S-mNotchIC having a fragment spanning the amino acid position 1704 to 2531 (Notch1C+3'UTR) was inserted into the EcoRI-XbaI site of PEF-BOS vector to generate pEF-Notch 1A (pEF-NotchΔE) (Yamamoto et al., JBC 276 (48): 45031-45040, 2001) (FIG. 3).

==Construction of a Reporter System Using Lentivirus==

Figure 4:
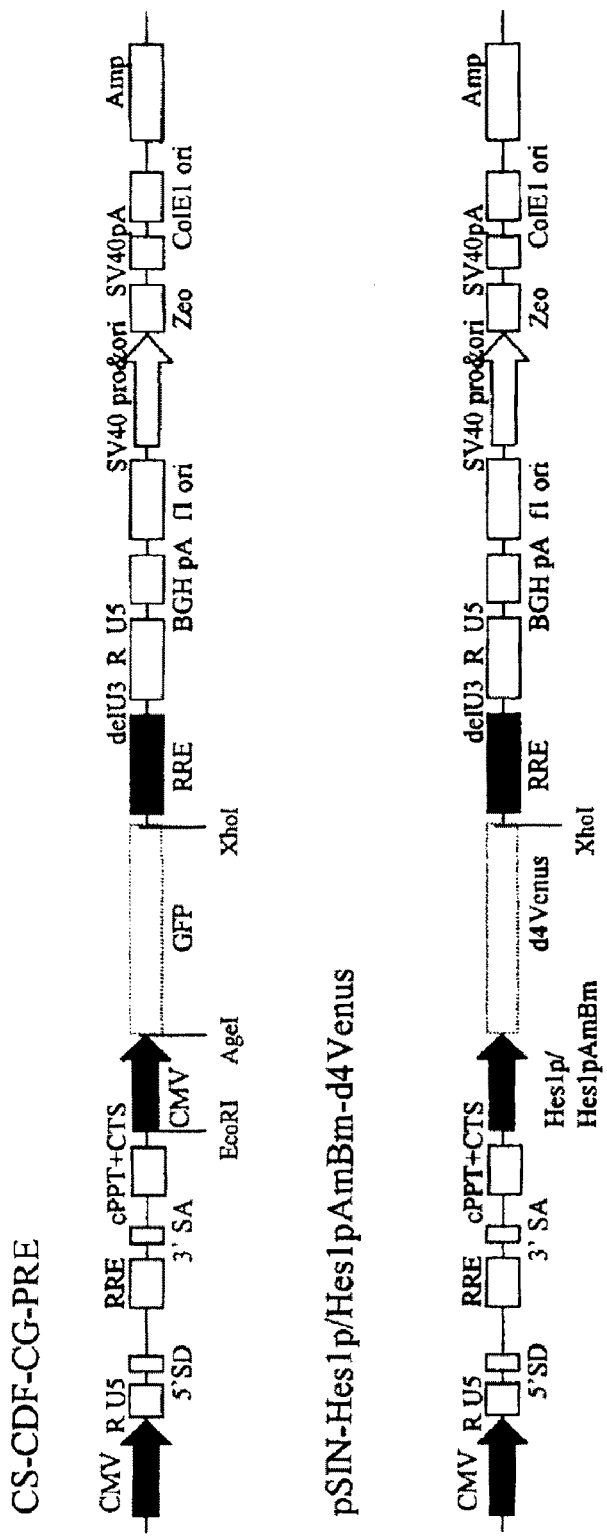
FIG. 4 shows the restriction maps of CS-CDF-CGF-PRE, pSIN-Hes1 p-d4Venus, and pSIN-Hes1 pAmBm-d4Venus used in the Example according to the present invention.

Each of an EcoRI-XhoI fragment of CS-CDF-CGF-PRE (Miyoshi et al., J Virol. 72, 8150-8157, 1998), an AseIp-NotI fragment of Hes1 p-d4Venus, and a KpnI-NotI fragment of Hes1 pAmBm-d4Venus was blunt-ended and then fragments of Hes1 p-d4Venus and Hes1 pAmBm-d4Venus were inserted into CS-CDF-CGF-PRE to generate pSIN-Hes1 p-d4Venus and pSIN-Hes1 pAmBm-d4Venus, respectively (FIG. 4).

Next, by using Hes1 or Hes1pAmBm expression vector, a lentivirus was obtained by the method described in the literature (Miyoshi et al., J. Virol. vol. 72, 8150-8157, 1998). A brief description is given below. First, HEK 293T cells were cultured in DMEM containing 10% FBS in 15-cm dishes. When cells proliferated and reached to about 80% confluency on the dish, 45.9 μg of vector DNA, 32.4 μg of MDLg/pRRE, 20.25 μg of pCMV-VSV-F (VSV-F expression vector) and 13.5 μg of PRSV-Rev (Rev expression vector) per dish was introduced into the cells by the calcium phosphate co-precipitation method. After 16 hours, the medium was changed, 15.5 ml of DMEM containing 10% FBS. After 48 hours, the supernatant was recovered, filtered through a 0.45 μm filter and virus was concentrated by ultra-centrifugation. The concentrated virus solution was diluted with 100 μl of serum-free culture medium.

==Each Promoter's Response to the Activation of the Notch Signaling==

By using the transient assay in cultured cells, the response of each of the promoters on pHes1 p-d4Venus and pHes1 pAmBm-d4Venus to the activation of the Notch signaling was examined.

Figure 5:
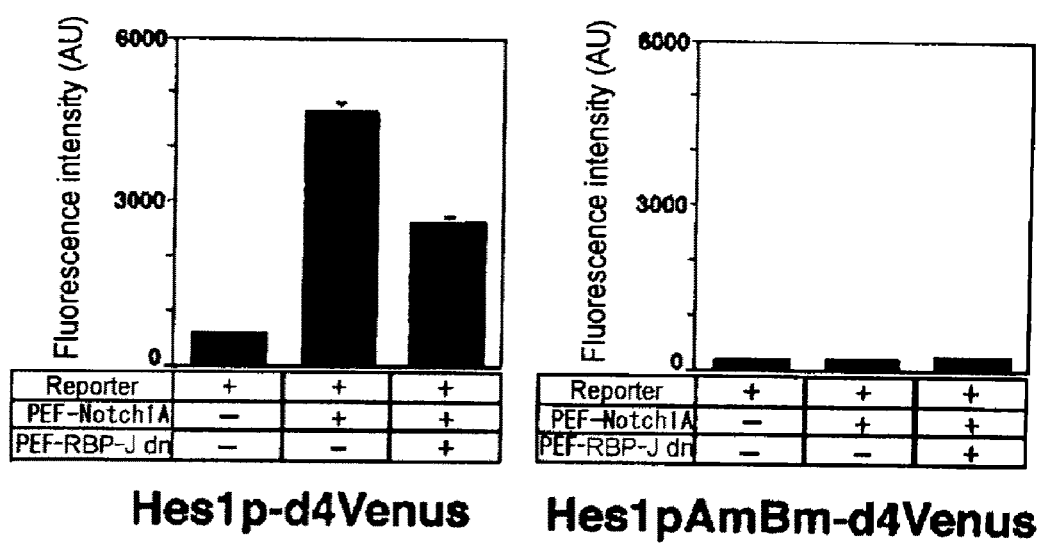
FIG. 5 shows the results obtained by examining responses of promoters in pHes1 p-d4Venus and pHes1 pAmBm-d4Venus to the activation of the Notch signaling by using transient assay in cultured cells in the Example according to the present invention.

HEK 293T cells were cultured under the conditions of 37° C. and 5% CO2 using DMEM containing 10% FCS. Using Lipofectamine Plus (Gibco-BRL), pHes1 p-d4Venus or pHes1 pAmBm as a reporter, and pPEF-Notch 1A for activation of the Notch signaling, were introduced according to the attached protocol. Additionally, an experiment in which only the reporter was introduced without introducing PEF-Notch was also conducted as a negative control. Twenty four hours after lipofection, cells were lysed and the fluorescence intensity was measured by using CytoFluor (PerSeptive Biosystem). The results are shown in FIG. 5.

When pHes1 p-d4Venus was used as the reporter, the activation of the Notch signaling increased the fluorescence intensity up to about 9-fold, whereas when pHes1 pAmBm-d4Venus was used as the reporter, the activation of Notch did not change the fluorescence intensity. In other words, the pHes1p promoter responded to the activation of the Notch signaling, whereas the Hes1pAmBm promoter did not respond to the activation of the Notch signaling. Therefore, in gene-transferred cells in which the Notch signaling is activated, fluorescent signals generated by pHes1 p-d4Venus can be observed, whereas fluorescent signals by pHes1 pAmBm-d4Venus cannot be observed.

==Specificity of a Mutated Hes-1 Promoter to the Notch Signaling==

To examine the specificity of the Hes1pAmBm promoter, a mutated Hes-1 promoter, to the Notch signaling, it was examined whether the activation of a reporter by the Notch signaling was inhibited by a γ-secretase inhibitor known to suppress the activation of the Notch signaling by suppressing the cleavage of the intracellular domain of Notch-1.

First, a telencephalon was excised from a day 14 mouse embryo and dissociated by pipetting. The telencephalon cells were incubated in MHM (Kawaguchi et al., Mol Cell Neurosci. 17, 259-73, 2001) supplemented with EGF (final concentration: 20 ng/ML) and bFGF (final concentration: 20 ng/ML) at a cell density of $1 \times 10^6$ cells/ml.

After three hours of incubation, a lentivirus having pSIN-Hes1 p-d4Venus or pSIN-Hes1 pAmBm-d4Venus was added to the medium at a MOI of 50 and the cells were further incubated for 24 hours.

Figure 6:
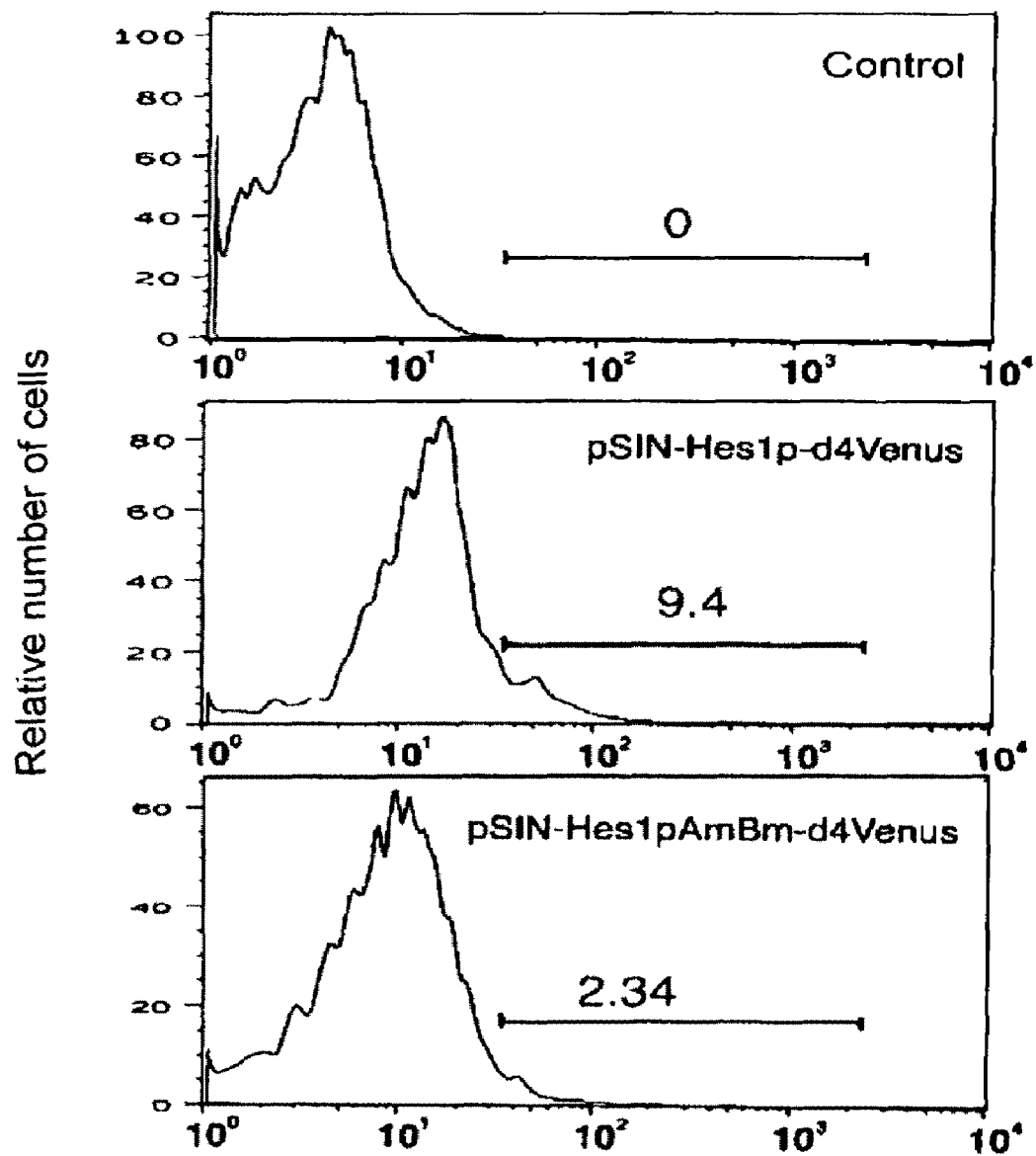
FIG. 6 shows the results of separation and analysis of cells using fluorescent signals obtained from cultured telencephalon cells administered with lentivirus having pSIN-Hes1 p-d4Venus or pSIN-Hes1 pAmBm-d4Venus in the Examples according to the present invention.

Aggregated cortical cells were re-dissociated by pipetting, re-suspended in MHM containing 1 μg/ml propidium iodide (PI), and filtered through a nylon mesh (40-μm pore size). The cells were separated and analyzed by using a FACSVantage SE flow cytometer (Becton-Dickinson) or a MOFLO (Dako Cytomation, Inc.). The results are shown in FIG. 6.

Infection with the lentivirus having only a rat minimal promoter, as a negative control, did not result in detection of fluorescence, whereas infection with the lentivirus having pSIN-Hes1 p-d4Venus or pSIN-Hes1 pAmBm-d4Venus resulted in detection of cells emitting fluorescence.

Figure 7:
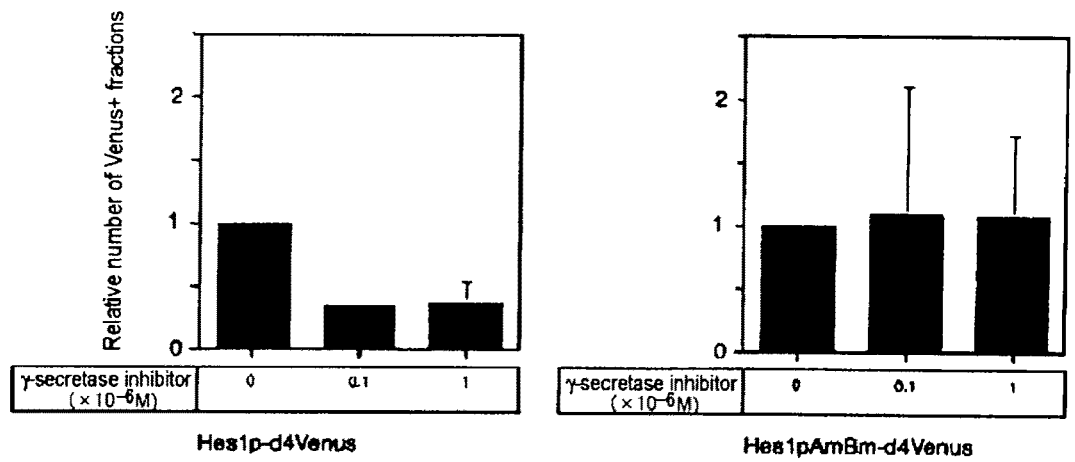
FIG. 7 shows the results of separation and analysis of cells using fluorescent signals obtained from telencephalon cells which were infected with lentivirus having pSIN-Hes1 p-d4Venus or pSIN-Hes1 pAmBm-d4Venus and then added with a γ-secretase inhibitor and dissociated in the Examples according to the present invention.

Then, 1 μM γ-secretase inhibitor was added to the telencephalon cells infected with the lentivirus having pSIN-Hes1 p-d4Venus or pSIN-Hes1 pAmBm-d4Venus and after 12 to 24 hours, the cells were dissociated, and separated and analyzed by flow cytometry in the same manner described above. The results are shown in FIG. 7.

The telencephalon cells infected with the lentivirus having pSIN-Hes1 p-d4Venus had sensitivity to the γ-secretase inhibitor, and their fluorescent signals were suppressed at a concentration of $1 \times 10^{-7}$ M. In contrast, the telencephalon cells infected with the lentivirus having pSIN-Hes1 pAmBm-d4Venus exhibited resistance to the γ-secretase inhibitor and suppression of fluorescent signals was not observed even at a concentration of $1 \times 10^{-6}$ M. It was thus found that the Hes1pAmBm promoter, the mutated promoter, is not influenced by the activation of the Notch signaling.

==Detection of the Activation of the Notch Signaling in Mouse Brain==

Cells in which the Notch signaling is activated were detected by introducing a fluorescent protein expression reporter into the brain of mouse embryos exo utero. The details are described as follows. It should be noted that pHes1 p-d4Venus or pHes1 pAmBm-d4Venus was used as the fluorescent protein expression reporter, and that pCXN2-mRFP (modified red fluorescent protein), which is expressed in all cells, was added to make up 20% of total DNA.

Figure 8:
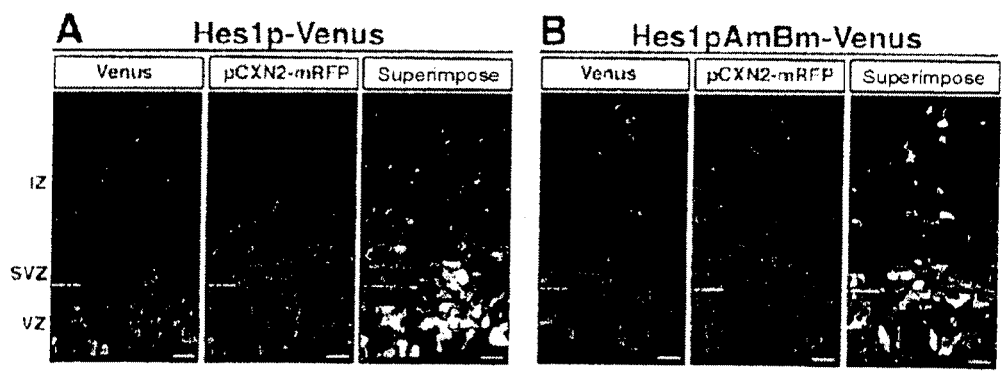
FIGS. 8A and 8B show the results of detection of the activation of the Notch signaling in mouse brains in the Example according to the present invention.

First, day 14 pregnant mice (ICR) were anesthetized, and their abdomen was excised to expose the uterus. The myometrium opposite to the placenta was longitudinally incised so as not to damage the embryo and placenta, and the day 14 embryo attaching to the placenta was removed intact. After injection of 1 μl of DNA solution (concentration: 5 mg DNA/ml PBS) into the left lateral ventricle of the telencephalon, the embryo was covered with the extra embryonic membrane and pinched between forceps electrodes. Using an electroporator (CUY21EDIT, Napa Gene), a rectangular pulse with a voltage of 25 V was applied 8 times at an interval of 950 ms. The treated embryo was returned to the abdominal cavity without suturing the uterine wall, and the abdominal cavity was filled with PBS warmed to 37° C. Then, the abdominal wall and epidermis were sutured. After 48 hours, the pregnant mice underwent laparotomy and the embryo was removed and fixed with 4% formaldehyde solution. The brain was removed and submerged in 20% sucrose solution overnight. Then sections with thickness of 12 μm were prepared. The results are shown in FIG. 8.

Most of the red fluorescence from pCXN2-mRFP was observed in the ventricular zone (VZ); among them, the cells emitting green fluorescence from pHes1 p-d4Venus had a characteristic radial fibers extending from the ventricle side to the cranial pia mater side. In contrast, cells emitting green fluorescence from pHes1 pAmBm-d4Venus had no radial fibers; most of such cells were observed in the subventricular zone (SVZ) and some were observed in the intermediate zone (IZ).

Thus, by using the method for detecting the activation of the Notch signaling according to the present invention, it was revealed that, in day 14 to 16 mouse embryos, the Notch signaling is specifically activated mainly in cells having radial fibers extending from the ventricle side to the cranial pia mater side. Further, it was revealed that in the SVZ and IZ, cells are present, in which the expression of HES1 is suppressed in a manner dependent on the RBP-J binding sequence.

INDUSTRIAL APPLICABILITY

According to the present invention, detection methods of Notch signaling activation for detecting the activation of Notch signaling in living cells conveniently, as well as transgenic cells and fluorescent protein expression reporters to be used for such detection, can be provided.

What is claimed is:

1. An in vitro method for identifying a cell in which Notch signaling is activated, comprising the steps of:
   providing a gene-transferred cell comprising a first fluorescent protein (FP) gene and a second FP gene wherein the first fluorescent protein gene encodes the first fluorescent protein and is controlled by a wild-type Hes-1 gene promoter and the second fluorescent protein gene encodes the second fluorescent protein and is controlled by a mutated Hes-1 gene promoter that does not respond to an activated Notch protein, wherein the first fluorescent protein and the second fluorescent protein are different;
   comparing the expression of the first fluorescent protein and the second fluorescent protein in the gene-transferred cell; and
   identifying, as a cell in which the Notch signaling is activated, a cell in which expression of the first fluorescent protein is observed but expression of the second fluorescent protein is not observed.

2. The method of claim 1, wherein at least one of the first fluorescent protein gene and the second fluorescent protein gene is inserted into a Hes-1 locus and controlled by an endogenous Hes-1 gene promoter in the Hes-1 locus.

3. The method of claim 1, wherein at least one of the first fluorescent protein gene and the second fluorescent protein gene is controlled by an exogenous Hes-1 gene promoter inserted into a genome of the cell comprising the fluorescent protein gene.

4. The method of claim 1, wherein the mutated Hes-1 gene promoter comprises a mutation in RBP-J binding site(s).

5. The method of claim 1, wherein at least one of the first fluorescent protein and the second fluorescent protein is Venus.

6. The method of claim 1, wherein an amino acid sequence rich in proline (P), glutamic acid (E), serine (S) and threonine (T) (a PEST sequence) is fused with at least one fluorescent protein of the first fluorescent protein and the second fluorescent protein.

7. An isolated gene-transferred cell comprising:
   a first fluorescent protein (FP) gene controlled by a wild-type Hes-1 gene promoter; and
   a second fluorescent protein gene controlled by a mutated Hes-1 gene promoter, wherein the mutated promoter is not controlled by an activated Notch protein, wherein the first fluorescent protein and the second fluorescent protein are different.

8. The isolated gene-transferred cell of claim 7, wherein at least one fluorescent protein gene of the first fluorescent protein gene and the second fluorescent protein gene is inserted into a Hes-1 locus and controlled by an endogenous Hes-1 gene promoter in the Hes-1 locus.

9. The isolated gene-transferred cell of claim 7, wherein at least one fluorescent protein gene of the first fluorescent protein gene and the second fluorescent protein gene is controlled by an exogenous Hes-1 gene promoter inserted into a genome of the cell comprising the fluorescent protein genes.

10. The isolated gene-transferred cell of claim 7, wherein the mutated Hes-1 gene promoter comprises a mutation in RBP-J binding site(s).

11. The isolated gene-transferred cell of claim 7, wherein the fluorescent protein encoded by at least one fluorescent protein gene of the first fluorescent protein gene and the second fluorescent protein gene is Venus.

12. The isolated gene-transferred cell of claim 7, wherein a PEST sequence is fused with the fluorescent protein encoded by at least one fluorescent protein gene of the first fluorescent protein gene and the second fluorescent protein gene.

* * * * *

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Inventor: Okano, Hideyuki
      Inventor: Tokunaga, Akinori
      Inventor: Kohyama, Jun
      Inventor: Nakao, Keiko
<220> FEATURE:
<223> OTHER INFORMATION: primer 1

<400> SEQUENCE: 1
gattaatctc aggcgcgcgc ca                                      22

<210> SEQ ID NO 2
<211> LENGTH: 22
<212> TYPE: DNA
<213> ORGANISM: Artificial Sequence
<220> FEATURE:
<223> OTHER INFORMATION: primer 2

<400> SEQUENCE: 2
```

-continued

```
gaccggtgga tccgcttacg tc                                              22

<210> SEQ ID NO 3
<211> LENGTH: 375
<212> TYPE: DNA
<213> ORGANISM: Artificial Sequence
<220> FEATURE:
<223> OTHER INFORMATION: HES-1 promoter (wt)

<400> SEQUENCE: 3
gattaatctc aggcgcgcgc cattggccgc cagaccttgt gcctagcggc caatgggggg     60
gcgcagtcca cgagcggtgc cgcgtgtctc ttcctcccat tggctgaaag ttactgtggg    120
aaagaaagtt tgggaagttt cacacgagcc gttcgcgtgc agtcccagat atatatagag    180
gccgccaggg cctgcggatc acacaggatc tggagctggt gctgataaca gcggaatccc    240
ctgtctacct ctctccttgg tcctgggata gtgctaccga tcactaagta gccctaagac    300
tataataaac cttcaactgc tcagtagttt ttcttatgaa agtcaagtaa aaggacgtaa    360
gcggatccac cggtc                                                     375

<210> SEQ ID NO 4
<211> LENGTH: 375
<212> TYPE: DNA
<213> ORGANISM: Artificial Sequence
<220> FEATURE:
<223> OTHER INFORMATION: HES-1 promoter (mutated)

<400> SEQUENCE: 4
gattaatctc aggcgcgcgc cattggccgc cagaccttgt gcctagcggc caatgggggg     60
gcgcagtcca cgagcggtgc cgcgtgtctc ttcctcccat tggctgaaag ttactctgcg    120
aaagaaagtt tgggaagttt cactcgagcc gttcgcgtgc agtcccagat atatatagag    180
gccgccaggg cctgcggatc acacaggatc tggagctggt gctgataaca gcggaatccc    240
ctgtctacct ctctccttgg tcctgggata gtgctaccga tcactaagta gccctaagac    300
tataataaac cttcaactgc tcagtagttt ttcttatgaa agtcaagtaa aaggacgtaa    360
gcggatccac cggtc                                                     375
```